United States Patent [19]

Ogawa et al.

[11] Patent Number: 4,623,477

[45] Date of Patent: Nov. 18, 1986

[54] ESTER COMPOUNDS HAVING A PYRIMIDINE RING

[75] Inventors: Tetsuya Ogawa; Yasuyuki Goto; Kisei Kitano, all of Yokohamashi; Naoyuki Yoshida, Kamakurashi, all of Japan

[73] Assignee: Chisso Corporation, Osaka, Japan

[21] Appl. No.: 654,877

[22] Filed: Sep. 27, 1984

[30] Foreign Application Priority Data

Oct. 7, 1983 [JP] Japan ................................ 58-187997
Nov. 18, 1983 [JP] Japan ................................ 58-217228

[51] Int. Cl.⁴ .......................... G09K 3/34; G02F 1/13; C07D 239/02
[52] U.S. Cl. ............................ 252/299.5; 252/299.61; 350/350 R; 544/315; 544/316; 544/318
[58] Field of Search .......... 252/299.5, 299.61, 299.63, 252/299.64; 350/350 R; 544/315, 316, 318

[56] References Cited

U.S. PATENT DOCUMENTS

| | | | |
|---|---|---|---|
| 4,001,137 | 1/1977 | Steinstrasser .................... | 252/299.64 |
| 4,113,647 | 9/1978 | Coates et al. .................... | 252/299.63 |
| 4,293,434 | 10/1981 | Deutscher et al. ............. | 252/299.63 |
| 4,311,610 | 1/1982 | Zaschke et al. ................. | 252/299.61 |
| 4,349,452 | 9/1982 | Osman et al. .................... | 252/299.61 |
| 4,358,393 | 11/1982 | Zaschke et al. ................. | 252/299.61 |
| 4,438,268 | 3/1984 | Zaschke et al. ................. | 252/299.61 |
| 4,510,069 | 4/1985 | Eidenschink et al. .......... | 252/299.61 |
| 4,512,636 | 4/1985 | Andrews et al. ................ | 252/299.61 |

FOREIGN PATENT DOCUMENTS

| | | | |
|---|---|---|---|
| 149238 | 7/1985 | European Pat. Off. ....... | 252/299.61 |
| 3404116 | 8/1985 | Fed. Rep. of Germany ........................ | 252/299.61 |
| 3407013 | 9/1985 | Fed. Rep. of Germany ........................ | 252/299.61 |
| 105701 | 5/1974 | German Democratic Rep. .................................. | 252/299.63 |
| 145914 | 1/1981 | German Democratic Rep. .................................. | 252/299.61 |
| 56-32579 | 4/1981 | Japan .............................. | 252/299.61 |
| 58-121272 | 7/1983 | Japan .............................. | 252/299.61 |
| 60-109569 | 6/1985 | Japan .............................. | 252/299.61 |
| 2092169 | 8/1982 | United Kingdom ........... | 252/299.61 |

OTHER PUBLICATIONS

Zaschke, H., Advances in Liquid Crystal Research and Applications, Bata L. Ed., Perchmen Press, N.Y., pp. 1059–1074, (1981).

Green, D. C. et al., IBM Tech. Discl. Bull., vol. 15, No. 8, pp. 2467–2468, (1973).

*Primary Examiner*—Teddy S. Gron
*Attorney, Agent, or Firm*—Leydig, Voit & Mayer

[57] ABSTRACT

Ester compounds having a pyrimidine ring, using as their raw material, substituted pyrimidinols in place of expensive p-substituted phenols, and also useful as a material for liquid crystal display elements are provided which esters are expressed by the general formula

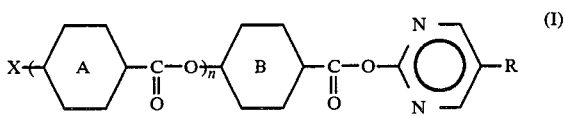

wherein R represents an alkyl or alkoxy group of 1 to 10 carbon atoms; X represents a halogen atom of F, Cl or Br, cyano group or an alkyl or alkoxy group of 1 to 10 carbon atoms;

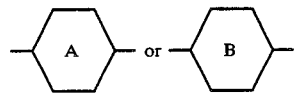

represents

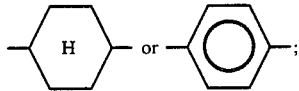

and n is 0 or 1.

28 Claims, No Drawings

ESTER COMPOUNDS HAVING A PYRIMIDINE RING

BACKGROUND OF THE INVENTION

1. Field of the Invention

This invention relates to novel organic compounds, and more particularly it relates to novel ester compounds useful as a component for liquid crystal materials.

2. Description of the Prior Art

As is well known, liquid crystalline compounds have been used for various display means, utilizing the dielectric anisotropy and the refractive anisotropy in their liquid crystalline phases. These display means include liquid crystal display elements employing the electro-optic effect of liquid crystals, those the thermo-optic effect of liquid crystals, those employing other optic effects of liquid crystals, etc., and conjointly with technical advances in electronics, a large number of liquid crystal compounds have been used for liquid crystal display elements having applied electric field effects, such as twisted nematic effect, guest-host effect, etc.

As to these liquid crystal materials, there is no single compound which endures practical use as regards various characteristics such as mesomorphic range, operating voltage, response performance, etc.; hence, at present, several kinds of liquid crystal compounds or non-liquid crystal compounds have been blended together to obtain materials which are endurable to practical use.

Heretofore, among p-substituted phenyl esters of benzoic acid, p-substituted benzoic acids, cyclohexane-carboxylic acid, 4-substituted cyclohexane-1-carboxylic acids, etc., many of such esters have been highly evaluated as materials for various liquid crystal display means, etc. utilizing their liquid crystalline properties.

However, p-substituted phenols as one of the raw materials for preparing the above esters are not readily available, and have been prepared from phenol via several reaction steps, and moreover the yield of the substituted phenols is notably reduced because of the specific reactivity of substituted benzenes; hence they are expensive raw materials.

The present inventors have made extensive research on ester compounds using as their raw material, substituted pyrimidinols in place of expensive p-substituted phenols, and as a result, have found that esters of 5-substituted pyrimidin-2-ols can be prepared with a high yield and are very useful as raw materials for liquid crystal elements.

The object of the present invention is to provide novel ester compounds which are applicable to similar uses to those of conventional phenyl esters and yet can be prepared with a much higher yield.

SUMMARY OF THE INVENTION

The present invention has the following first aspect:
(1) Ester compounds having a pyrimidine ring expressed by the general formula

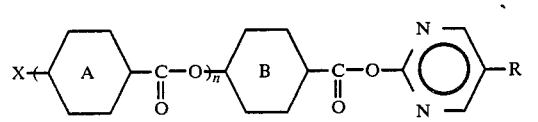

wherein R represents an alkyl or alkoxy group of 1 to 10 carbon atoms; X represents a halogen atom of F, Cl or Br, a cyano group or an alkyl or alkoxy group of 1 to 10 carbon atoms;

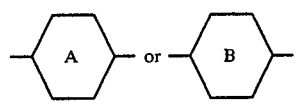

represents

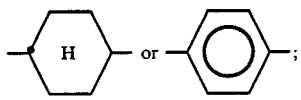

and n is 0 or 1.

The above item (I) has the following embodiments (2)~(4):

(2) 5-Substituted-pyrimidin-2-yl substituted carboxylates expressed by the general formula

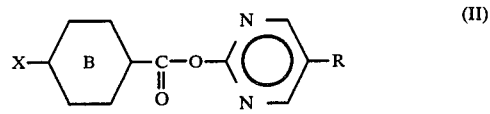

wherein R, X and

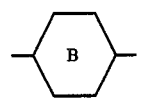

are as defined above.

(3) 5-Substituted-pyrimidin-2-yl substituted carboxylates expressed by the general formula

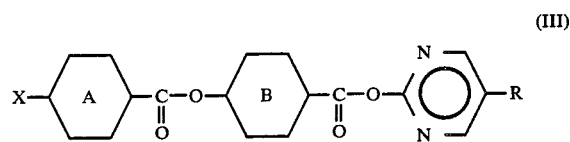

wherein R, X,

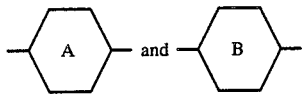

are as defined above.

(4) 5-Substituted-pyrimidin-2-yl 4'-substituted benzoates expressed by the general formula

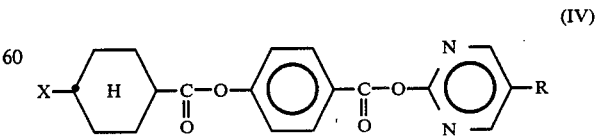

wherein R and X each represent an alkyl or alkoxy group of 1 to 10 carbon atoms.

The present invention has the following second aspect:

(5) Liquid crystal compositions containing at least one kind of the ester compounds having a pyrimidine ring expressed by the general formula (I) described in the above item (I).

DETAILED DESCRIPTION OF THE PREFERRED EMBODIMENTS

The raw materials used for the ester compounds of the present invention are not expensive compounds such as p-substituted-phenols, but compounds easily prepared from urea and aldehydes. These compounds may be prepared via the following pathway as expressed by chemical reaction equations:

$$R-CH_2CHO + (CH_3)_2NCHO \longrightarrow (CH_3)_2NCH=\underset{\underset{R}{|}}{C}-CHO \quad (A)$$

$$(CH_3)_2NCH=\underset{\underset{R}{|}}{C}-CHO + (NH_2)CO \longrightarrow \quad (B)$$

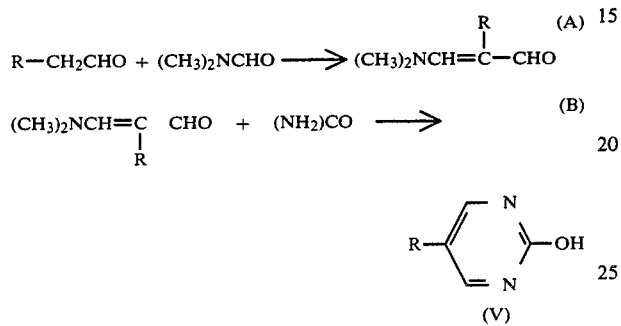

(V)

The above reaction equation (A) is referred to as Vilsmeir Reaction. The reaction of equation (B) is a conventional condensation reaction.

The compounds of the formula (I) of the present invention may be easily prepared according to the esterification reaction between a 5-substituted pyrimidin-2-ol of the above formula (V) and a carboxylic acid of the formula (VI) or a carboxylic acid chloride of the formula (VII), each shown below.

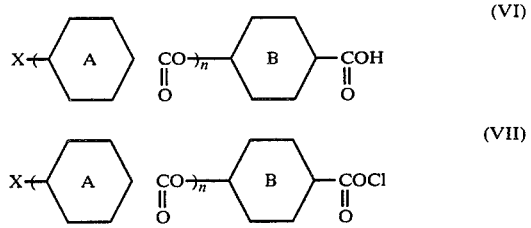

Many of the ester compounds of the present invention have a liquid crystalline phase, and by blending these with other liquid crystal compounds, it is possible to reduce the driving voltage of liquid crystal cells using the resulting compositions. Further, among the ester compounds, even those which exhibit no liquid crystalline phase exhibit a similar effectiveness when added to liquid crystal compositions.

The present invention will be more concretely described by way of Examples, but it is not construed to be limited thereby.

EXAMPLE 1

Preparation of 5-hexylpyrimidin-2-yl p-hexyloxybenzoate

While commercially available urea (6.0 g, 0.1 mol) and α-hexyl-β-dimethylaminoacrolein (18.3 g, 0.1 mol) were mixed with ethanol (70 ml) with stirring, conc. hydrochloric acid (50 ml) was added dropwise to the resulting solution, followed by heating under reflux for 1.5 hours, allowing the reaction mixture to stand at −20° C. for 16 hours to deposit crystals, and filtering off and drying the crystals to obtain 5-hexylpyrimidin-2-ol hydrochloride (yield: 97%). This hydrochloride was dissolved in pure water (30 ml), followed by adding dropwise 2N-NaOH aqueous solution, adjusting the pH of the mixture between 6~7 to deposit pale yellow crystals, filtering off the crystals and recrystallizing from a mixed solvent of n-heptanol and methanol to obtain 5-hexylpyrimidin-2-ol (8.4 g) (yield 48%).

This 5-hexylpyrimidin-2-ol (1.8 g, 10 mmol) was dissolved in pyridine (2 ml), followed by adding dropwise to the solution, a toluene solution (30 ml) of p-hexyloxybenzoyl chloride (2.4 g, 10 mmol), stirring at 50° C. for 4 hours, further adding toluene (50 ml) to the reaction mixture to carry out extraction, washing the toluene layer twice with 6N-HCl aqueous solution (30 ml), further washing 5 times with 2N-NaOH aqueous solution (40 ml), washing with pure water until the aqueous layer became pH 7, drying the toluene layer over anhydrous Na₂SO₄ and distilling off toluene to obtain raw crystals (3.1 g) (yield 81%), which were then purified by activated alumina chromatography (solvent: toluene) and recrystallized from ethanol to obtain 5-hexyl-pyrimidin-2-yl p-hexyloxybenzoate (2.2 g) (yield 58%). This compound exhibited liquid crystallinity and as to their phase transition points, C-N point was 28.4° C. and N-I point was 35° C.

EXAMPLES 2~9

Compounds prepared as in Example 1, their yields and values of physical properties are shown in Table 1 together with the results of Example 1.

TABLE 1

| | In formula (I) | | | | | Phase transition point* (°C.) | | |
|---|---|---|---|---|---|---|---|---|
| Example | R | X | A | B | n | Preparation yield | C | N | I |
| 1 | nC₆H₁₃ | nC₆H₁₃O | — | ⌬ | 0 | 58 | · 28.4 · 35.0 · |
| 2 | nC₆H₁₃ | CH₃O | — | ⌬ | 0 | 63 | · 47.0 — · |

TABLE 1-continued

| Example | R | X | In formula (I) A | B | n | Preparation yield | Phase transition point* (°C.) C | N | I |
| --- | --- | --- | --- | --- | --- | --- | --- | --- | --- |
| 3 | nC₅H₁₁ | CH₃O | — | phenyl | 0 | 62 | · | 56.4 | — |
| 4 | nC₆H₁₃ | C₂H₅ | — | phenyl | 0 | 30 | · | 51.5 | — · |
| 5 | nC₃H₇ | C₂H₅ | — | phenyl | 0 | 51 | · | 80.9 | — · |
| 6 | nC₆H₁₃ | nC₅H₁₁O | — | cyclohexyl (H) | 0 | 83 | · | 75.3 | — · |
| 7 | nC₆H₁₃ | nC₄H₉ | — | cyclohexyl (H) | 0 | 11 | · | 104.9 | — · |
| 8 | nC₆H₁₃ | F | — | phenyl | 0 | 90 | · | 44.6 | — · |
| 9 | nC₅H₁₁ | NC | — | phenyl | 0 | 73 | · | 79.2 | — · |

*C, N and I in the column of phase transition point represent crystalline and nematic phases and isotropic liquid phase, respectively, the symbol · represents that the phase is present and the numeral figure succeeding thereto represents a transition temperature from the phase to a phase on its right side. The symbol — represents that the phase is absent.

EXAMPLE 10

Preparation of 5-hexylpyrimidin-2-yl p-(trans-4-hexylcyclohexylcarbonyloxy)-benzoate A solution of p-(trans-4-hexylcyclohexylcarbonyloxy)-benzoyl chloride (3.9 g) dissolved in toluene was added to a solution of 5-hexylpyrimidin-2-ol (1.0 g) in pyridine (10 ml), followed by stirring at 60° C. for 2 hours, allowing the mixture to stand at room temperature overnight, adding water and toluene to the reaction mixture, separating the toluene layer containing the reaction product, washing the toluene solution twice with 6NHCl (30 ml), washing with water, washing 5 times with 2N NaOH (100 ml), finally washing with water till the washing water became neutral, drying the resulting toluene solution, distilling off low boiling mixture of solvent, etc. under reduced pressure, and recrystallizing crystals obtained from the residue from n-heptanol solvent to obtain the objective compound (2.0 g) (yield 73%), which had a C-N point of 53.3° C. and a N-I point of 125.3° C.

EXAMPLE 11

Example 10 was repeated except that 5-hexylpyrimidin-2-ol as one of the raw materials was replaced by 5-pentylpyrimidin-2-ol to prepare 5-pentylpyrimidin-2-yl p-(trans-4-hexylcyclohexylcarbonyloxy)-benzoate (yield 49%), which had a C-N point of 70.5° C. and a N-I point of 146.3° C.

EXAMPLE 12

(Application example)

A liquid crystal mixture (A) composed of trans-4-propyl-(4-cyanophenyl)cyclohexane 30% by weight, trans-4-pentyl-(4-cyanophenyl)cyclohexane 40% by weight, and trans-4-heptyl-(4-cyanophenyl)cyclohexane 30% by weight, has a N-I point of 52.1° C., a viscosity at 20° C. of 23.4 cp, a dielectric anisotropy value (hereinafter abbreviated to Δε) of 11.2 and an optical anisotropy value (hereinafter abbreviated to Δn) of 0.119. A liquid crystal cell composed of two opposed substrates each having a transparent electrode of stannic oxide coated with silicon dioxide and subjected to rubbing treatment, and having a distance between the electrodes of 10 μm, was prepared. The above liquid crystal composition (A) was sealed in the above cell. The characteristics of the resulting cell was measured at 20° C. to give a threshold voltage (hereinafter abbreviated to Vth) of 1.55 V and a saturation voltage (hereinafter abbreviated to Vsat) of 2.15 V.

5-Hexylpyrimidin-2-yl 4-(trans-p-hexylcyclohexyl-carbonyloxy)-benzoate (5 parts by weight) of Example 10 of the present invention was dissolved in the above liquid crystal composition (A) (95 parts by weight). The N-I point of the resulting composition rose to 54.3° C. It had a viscosity at 20° C. of 26.3 cp, a Δε of 11.0 and a Δn of 0.116. Further, the Vth and Vsat declined to 1.43 V and 1.98 V, respectively.

EXAMPLE 13

(Application example)

5-Pentylpyrimidin-2-yl-p-(trans-4-hexylcyclohexyl-carbonyloxy)-benzoate (5 parts by weight) of the present invention was dissolved in the liquid crystal mixture (A) (95 parts by weight) having the same composition as in Example 12. The resulting composition was measured in the same manner as in Example 12. As a result the N-I point rose to 54.2° C. The Δε was 11.0, the Δn, 0.115, the viscosity, 25.7 cp. The Vth and Vsat lowered down to 1.42 V and 1.93 V, respectively.

What we claim is:

1. Ester compounds having a pyrimidine ring expressed by the general formula

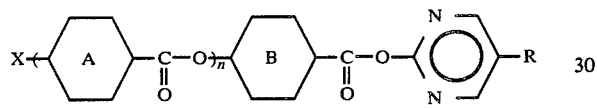

wherein R represents an alkyl or alkoxy group of 1 to 10 carbon atoms; X represents a halogen atom of F, Cl or Br, a cyano group or an alkyl or alkoxy group of 1 to 10 carbon atoms;

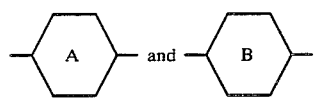

represent

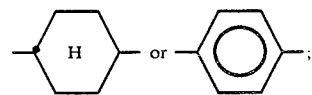

n is 0 or 1; and when n is 1,

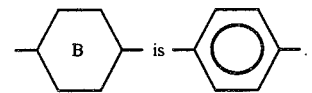

2. 5-Substituted-pyrimidin-2-yl substituted carboxylates expressed by the general formula

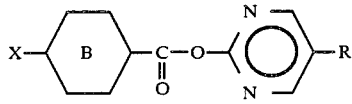

wherein R represents an alkyl or alkoxy group of 1 to 10 carbon atoms; X represents a halogen atom of F, Cl or Br, a cyano group or an alkyl or alkoxy group of 1 to 10 carbon atoms and

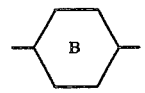

represents

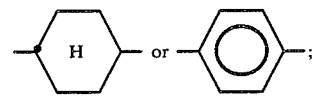

and when X is a cyano group or a halogen atom,

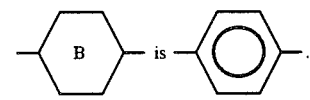

3. 5-Substituted-pyrimidin-2-yl substituted carboxylates expressed by the general formula

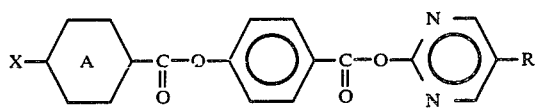

wherein R represents an alkyl or alkoxy group of 1 to 10 carbon atoms; X represents a halogen atom of F, Cl or Br, a cyano group or an alkyl or alkoxy group of 1 to 10 carbon atoms;

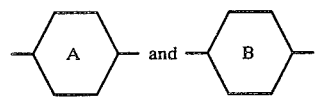

represent

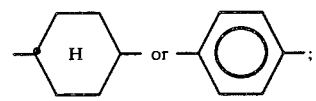

and when X is a cyano group or a halogen atom

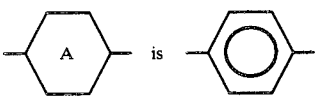

4. A liquid crystal composition comprising at least one first substance having liquid crystal properties and at least one second substance comprising an ester compound having a pyrimidine ring expressed by the general formula

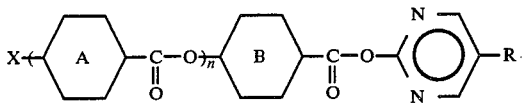

wherein R represents an alkyl or alkoxy group of 1 to 10 carbon atoms; X represents a halogen atom of F, Cl or Br, a cyano group or an alkyl or alkoxy group of 1 to 10 carbon atoms;

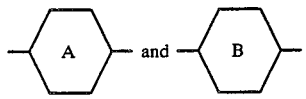

represent

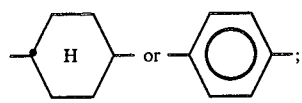

n is 0 or 1, and when n is 1,

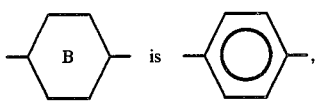

said at least one second substance is present in an amount effective to enhance said liquid crystal properties.

5. 5-Substituted-pyrimidin-2-yl 4'-substituted-benzoates expressed by the general formula

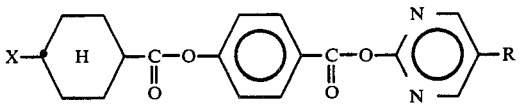

wherein R and X each represent an alkyl or alkoxy group of 1 to 10 carbon atoms.

6. An ester compound according to claim 1 wherein R is a propyl, pentyl or hexyl group.

7. An ester compound according to claim 1 wherein X is an ethyl, butyl, hexyl, methoxyl, pentoxyl, or hexoxyl group.

8. A pyrimidinyl substituted carboxylate according to claim 2 wherein R is a propyl, pentyl or hexyl group.

9. A pyrimidinyl substituted carboxylate according to claim 2 wherein X is an ethyl, butyl, hexyl, methoxyl, pentoxyl, or hexoxyl group.

10. A pyrimidinyl substituted carboxylate according to claim 2 comprising 5-hexylpyrimidin-2-yl p-hexoxybenzoate.

11. A pyrimidinyl substituted carboxylate according to claim 2 comprising 5-hexylpyrimidin-2-yl p-methoxybenzoate.

12. A pyrimidinyl substituted carboxylate according to claim 2 comprising 5-pentylpyrimidin-2-yl p-methoxybenzoate.

13. A pyrimidinyl substituted carboxylate according to claim 2 comprising 5-hexylpyrimidin-2-yl p-ethylbenzoate.

14. A pyrimidinyl substituted carboxylate according to claim 2 comprising 5-propylpyrimidin-2-yl p-ethylbenzoate.

15. A pyrimidinyl substituted carboxylate according to claim 2 comprising 5-hexylpyrimidin-2-yl trans-4-pentoxycyclohexanecarboxylate.

16. A pyrimidinyl substituted carboxylate according to claim 2 comprising 5-hexylpyrimidin-2-yl trans-4-butylcyclohexanecarboxylate.

17. A pyrimidinyl substituted carboxylate according to claim 2 comprising 5-hexylpyrimidin-2-yl p-fluorobenzoate.

18. A pyrimidinyl substituted carboxylate according to claim 2 comprising 5-pentylpyrimidin-2-yl p-cyanobenzoate.

19. A pyrimidinyl substituted carboxylate according to claim 3 wherein R is a propyl, pentyl or hexyl group.

20. A pyrimidinyl substituted carboxylate according to claim 3 wherein X is an ethyl, butyl, hexyl, methoxyl, pentoxyl, or hexoxyl group.

21. A pyrimidinyl substituted benzoate according to claim 5 wherein R is a pentyl or hexyl group and X is a hexyl group.

22. A pyrimidinyl substituted benzoate according to claim 5 comprising 5-hexylpyrimidin-2-yl p-(trans-4-hexylcyclohexylcarbonyloxy)benzoate.

23. A pyrimidinyl substituted benzoate according to claim 5 comprising 5-pentylpyrimidin-2-yl p-(trans-4-hexylcyclohexylcarbonyloxy)benzoate.

24. A liquid crystal composition according to claim 4 wherein R is a propyl, pentyl or hexyl group.

25. A liquid crystal composition according to claim 4 wherein X is an ethyl, butyl, hexyl, methoxyl, pentoxyl, or hexoxyl group.

26. A liquid crystal composition according to claim 4, comprising, by weight, 5 percent of 5-hexylpyrimidin-2-yl p-(trans-4-hexylcyclohexylcarbonyloxy)benzoate and 95 percent of a liquid crystal mixture comprising, by weight, 30 percent trans-4-propyl(4-cyanophenyl)cyclohexane, 40 percent trans-4-pentyl(4-cyanophenyl)cyclohexane, and 30 percent trans-4-heptyl-(4-cyanophenyl)cyclohexane.

27. A liquid crystal composition according to claim 4 comprising, by weight, 5 percent of 5-pentylpyrimidin-2-yl p-(trans-4-hexylcyclohexylcarbonyloxy)benzoate and 95 percent of liquid crystal mixture comprising, by weight, 30 percent trans-4-propyl(4-cyanophenyl)cyclohexane, 40 percent trans-4-pentyl(4-cyanophenyl)cyclohexane, and 30 percent trans-4-heptyl(4-cyanophenyl)cyclohexane.

28. The liquid crystal composition according to claim 4 wherein when n is 0 and X is a cyano group or a halogen atom,

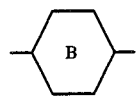

is phenylene.